United States Patent
Dubey et al.

(10) Patent No.: US 9,381,224 B2
(45) Date of Patent: Jul. 5, 2016

(54) PLANT BASED FORMULATION FOR THE PREVENTION AND MANAGEMENT OF METABOLIC SYNDROME AND CARDIOVASCULAR DISEASE MORTALITY RISK

(71) Applicants: Govind P. Dubey, Kattankulathur (IN); Aruna Agrawal, Varanasi (IN); Gurprit I. Singh, Bathinda (IN); Gurpreet S. Gill, Bathinda (IN); Shipra Dubey, Bathinda (IN); Rajesh Dubey, Bathinda (IN)

(72) Inventors: Govind P. Dubey, Kattankulathur (IN); Aruna Agrawal, Varanasi (IN); Gurprit I. Singh, Bathinda (IN); Gurpreet S. Gill, Bathinda (IN); Shipra Dubey, Bathinda (IN); Rajesh Dubey, Bathinda (IN)

(73) Assignees: Gurpreet Singh Gill, Bathinda (IN); Harinder Singh Gill, Punjab (IN)

( * ) Notice: Subject to any disclaimer, the term of this patent is extended or adjusted under 35 U.S.C. 154(b) by 131 days.

(21) Appl. No.: 14/468,281

(22) Filed: Aug. 25, 2014

(65) Prior Publication Data

US 2016/0051615 A1 Feb. 25, 2016

(51) Int. Cl.
*A01N 65/00* (2009.01)
*A61K 36/8945* (2006.01)
*A61K 36/37* (2006.01)
*A61K 36/185* (2006.01)

(52) U.S. Cl.
CPC ........... *A61K 36/8945* (2013.01); *A61K 36/185* (2013.01); *A61K 36/37* (2013.01)

(58) Field of Classification Search
CPC ..................................................... A61K 36/00
USPC ........................................................ 424/725
See application file for complete search history.

(56) References Cited

FOREIGN PATENT DOCUMENTS

CN            101104045     *  1/2008

* cited by examiner

*Primary Examiner* — Michael Meller
(74) *Attorney, Agent, or Firm* — Venable LLP; Keith G. Haddaway; David M. Klecyngier

(57) ABSTRACT

The invention relates to a plant based formulation for the prevention and management of Metabolic Syndrome and Cardiovascular disease mortality risk comprising an effective amount of a hydro-alcoholic extract of *Salacia parviflora*, *Tribulus terrestris* and *Dioscorea glabra*.

14 Claims, No Drawings

PLANT BASED FORMULATION FOR THE PREVENTION AND MANAGEMENT OF METABOLIC SYNDROME AND CARDIOVASCULAR DISEASE MORTALITY RISK

FIELD OF THE INVENTION

The present invention relates to a plant based formulation for the prevention and management of Metabolic Syndrome and Cardiovascular disease mortality risk, more specifically useful in for the prevention and management of insulin resistance, hypercholesterolemia, atherogenic dyslipidemia, vascular inflammation, obesity associated altered adipokines. However the test formulation may have potential role on leptin metabolism, adiponectin elevating property, insulin sensitivity enhancing activity and increasing the nitric oxide, plasminogen activator inhibitor-I, endothelin-1 and Sphingosine-1-phosphate reducing effects.

BACKGROUND OF THE INVENTION

Metabolic syndrome is one of the rapid growing health problems and has been the major risk factor for both diabetes and cardiovascular disease (CVD). Both genetic and environmental factors play a role in the development of metabolic syndrome.

The metabolic syndrome represents a combined occurrence of atherogenic dyslipidemia, insulin resistance, hypertension and obesity. It is established that obesity and metabolic syndrome significantly influence the onset of cardiovascular disorders particularly in presence of type-2 diabetes mellitus. Increasing incidence of obesity has markedly enhanced the prevalence of metabolic syndrome world wide. Pro-inflammatory and pro-thrombotic state, responsible for endothelial dysfunction is a common feature among metabolic syndrome cases. In metabolic syndrome the status of impaired glucose tolerance, insulin resistance, dyslipidemia and hypertension exhibits a pro-thrombotic state.

It is reported that about one quarter of adults and about nine percent of teenagers are having metabolic syndrome. Persons with metabolic syndrome are two times more at risk of developing heart disease and five times at risk of developing diabetes. The etiopathogenesis of metabolic syndrome is both genetic and environmental factors. Excess abdominal fat, defect in insulin action and energy storage are the major risk factors playing role in the occurrence of metabolic syndrome. According to the National Cholesterol Education Program of Adult Treatment Panel III (ATP-III) guidelines for identifying metabolic syndrome, the diagnosis is based upon the involvement of three or more of the components together like abdominal obesity, triglycerides, HDL-c, blood pressure and fasting glucose level.

Obesity play a major role in the development of metabolic syndrome. Obesity results from an imbalance between energy intake and energy expenditure. Both genetic as well as environmental factors are the predisposing factor for weight grain and causing obesity. Obesity management requires a drastic pharmacotherapy due to unsatisfactory results of diet control and exercise. Recently the anti-obesity agent Sibutramine an appetite suppressant and Orlistat an inhibitor of fat absorption, is being used for the treatment of metabolic syndrome.

Maximum attention has been focused on the identification and treatment of dyslipidemia associated with metabolic syndrome. The abnormality in lipid metabolism with abdominal fat accumulation is well defined. An increased number of small dense LDL particles is constant feature of dyslipidemia of abdominal adiposity as they are associated with insulin resistance, intra-abdominal fat and hypertension. LDL comprises a spectrum of particles that vary in size, density, chemical composition and atherogenic potentials. The presence of small dense cholesterol-depleted LDL particles is associated with an increased risk of mycordial infarction and further worsens due to severity of cardiovascular disease. Due to the mechanism the small dense LDL particles enter in to the arterial wall more easily bind to arterial wall proteoglycans more avidly and are susceptible to oxidative modification, leading to macrophage uptake all of which may contributing to increased atherogenesis.

The evaluation of apolipo-B in the metabolic syndrome can help in targeting patients for aggressive lipid-lowering therapy. High levels of LDL-c are generally accepted to be one of the strongest risk factors for cardiovascular disease. Insulin resistance is associated with increased numbers of small VLDL-c and LDL-c particles, reflected by higher apolipo-B levels, with decreased triglyceride to apolipo-B ratios compared with those in individuals with normal insulin sensitivity. Studies have shown that increased apolipo-B and apolipo-B-containing lipoproteins (VLDL-c and LDL-c) are related to an increased risk of cardiovascular disease found significantly higher in individuals with metabolic syndrome.

Evidence suggests an association between chronic inflammation, insulin resistance, obesity, type-2 diabetes mellitus and arthrosclerosis. Recently, workers have reported that chronic inflammatory process may enhance insulin resistance and impaired $\beta$-cell function which are the risk factors for the occurrence of diabetes.

A number of studies have indicated that obesity and insulin resistance are associated with higher levels of markers of inflammation and endothelial function. Thus the relationship between various inflammatory markers particularly c-reactive protein and interleukin-6 and risk of development of type-2 diabetes mellitus is well established. Adiponectin i.e. adipocyte derived hormone has potentiality to down regulate inflammatory responses and also to improve glucose tolerance and insulin resistance. Adiponectin is related to insulin resistance and adiposity in humans and it is protective against the risk of development of diabetes.

Recently adiponectin has been discovered as a potential agent derived from adipose tissue. Low plasma levels of adiponectin are associated with insulin resistance, obesity, atherosclerosis, dyslipidemia and ultimately results in coronary heart disease. This hormone has been shown to be a key regulator of insulin sensitivity in human being. Adiponectin is an adipose tissues derived glycoprotein totally secreted by adipose tissue. Circulating adiponectin activates the peroxisome, proliferators activated receptor (PPAR-$\alpha$) which are responsible for the regulation of glucose metabolism. Several workers have observed that hypo-adiponectenemia is a result of obesity induced, insulin resistance in adipose tissues. The molecular mechanism of insulin resistance specially in adipose tissues can only be understood from the study of endocrine regulation of energy metabolism and the role of various adipokines like leptin, ghrelin, adiponectin and resistin. All these adipokines are produced by adipose tissues. The biological effects of adiponectin in humans have been a subject of interests to the pharmacologist who are searching sub-specific targets who can regulate the abnormal anergy metabolism and can prevent the occurrence of insulin resistance, obesity and other related complications of metabolic syndrome. In case of insulin resistance plasma adiponectin is significantly less and is also associated with elevated levels of lipoprotein, glycemic index and dyslipidemia. It has been reported that adiponectin gene variants were one of the causes of obesity and insulin resistance.

The endothelial cells produce different variety of molecule that regulates its barrier function, and maintains the vascular homeostasis. From our observation it is apparent that the combined formulation specifically *Dioscorea glabra* maintains the vascular integrity by its local and central action. The Sphingosine-1-phosphate is derived from platelet and play an important role in maintaining endothelial barrier function which is one of the most complicated process.

There is an intimate association between obesity and inflammatory markers such as c-reactive protein (CRP) which has been repeatedly associated with increased risk of CVD. This association appears to mediate the progression to diabetes and CVD.

Insulin resistance may cause hypertension, however all patients with hypertension may not have metabolic abnormalities, nor does hypertension occur in all cases showing increased insulin level.

Further, reported that blood pressure falls when the dose of insulin is decreased in obese hypertensive patients with type-2 diabetes and increases when insulin treatment is begun in diabetic patients whose plasma glucose concentration are poorly controlled with oral agents.

The identification of large number of genetic markers particularly single nucleotide polymorphism is of clinical significance to launch preventive measures as well as to understand the susceptibility towards specific disease condition. The unsatisfactory achievements in the area of clinical diagnosis and therapy is due to insufficient studies on heterogeneity of human populations, late onset of diseases is of complex nature of disease and concomitant presence of confounding risk factors. Several genome scans have been carried out recently on metabolic syndrome. However, to identify disease genes and their etiologic genetic variants to explain disease phenotypes from biologic point of view is difficult. Many of these genes have been associated with metabolic syndrome in various ethnic populations. These candidate genes are mainly PPAR-γ, adiponectin, CD36, β-adrenergic receptors, insulin receptor, substrates, 11β-hydroxysteriod dehydrogenase type 1 (11β-HSD), CRP, TNF-α, calpain-10 (CAPN10), upstream transcription factor 1 and skeletal muscle glycogen synthase-1.

In brief, the adiponectin of susceptibility genes of metabolic syndrome and their, functional variants as well as the associated patho-physiological mechanisms are of importance as it makes us to design preventive strategies and targeted treatments.

Keeping the above facts in view it was proposed to develop a plant based safe drug beneficial in the management of cluster of clinical conditions i.e. obesity, insulin resistance, dyslipidemia, hypertension associated with metabolic syndrome. As all these are conventional CHD risk factors and aggregate at one place among individuals with metabolic syndrome are warranted for a drastic management strategy in order to prevent the risk of CHD mortality among metabolic syndrome patients.

Scientific evaluation of some of the Ayurvedic drugs have shown better efficacy over standard pharmacologic therapies with minimum or without any side effect. The successful management of metabolic syndrome is seldom possible with a single drug entity as it is a disease condition clustering a group of abnormalities. In Ayurvedic system of medicine a comprehensive description as well as prevention and management methods/procedures is given for obesity, diabetes and lipid disorders. Thus taking lead from Ayurvedic literature the present test formulation has been prepared and evaluated on scientific parameters involved with metabolic syndrome.

OBJECT OF THE INVENTION

The primary object of present invention is to propose/develop a plant based formulation which is safe and effective in the management of metabolic syndrome with the view to prevent/minimize the mortality due to coronary heart disease.

Another object of present invention is to propose a plant based formulation having potential role in the leptin metabolism as well as adiponectin enhancing property.

Further, object of this invention is to develop a plant based formulation beneficial in enhancing the insulin sensitivity among metabolic syndrome cases to prevent development of type-2 diabetes mellitus.

Still, another object of present invention is to reduce the increased level of apolipo-B including regulation of triglycerides and apolipo-B ratio.

Still, another object of present invention is to proposed a plant based medicine having blood pressure lowering effects as well as prevent the atherosclerotic process among metabolic syndrome patients.

Yet another object of the present invention is to preserve the vascular integrity by preventing the progression of atherosclerosis through Sphingosine-1-phosphate mediated signaling.

Another object of present invention is to propose a plant based formulation having potential role to prevent the development of endothelial dysfunction through its action on atherogenic dyslipidemia, leptin metabolism, plasminogen activator inhibitor (PAI), endothelin-1, pro-inflammatory cytokines including certain genetic markers playing role in metabolic syndrome.

The foregoing has outlined some of the pertinent objectives of the invention. These objectives should not be construed to be merely illustrative of some of the more prominent features and applications of the intended invention. Many other beneficial results can be obtained by applying the disclosed invention in a different manner or modifying the invention within the scope of disclosure.

Accordingly, other objectives and a full understanding of the invention and the detailed description of the preferred embodiment in addition to the scope of invention are to be defined by the claims undertaken.

These and other objects and advantages of the invention will be apparent from the ensuing description.

STATEMENT OF THE INVENTION

According to the invention, there is provided a plant based formulation for the prevention and management of Metabolic Syndrome and Cardiovascular disease mortality risk comprising an effective amount of a hydro-alcoholic extract of *Salacia parviflora, Tribulus terrestris* and *Dioscorea glabra*.

DETAILED DESCRIPTION OF THE INVENTION

At the outset of the description, which follows, it is to be understood that the ensuing description only illustrate a particular form of the invention. However, such a particular form is only an exemplary embodiment and the teaching of the invention are not intended to be taken restrictively.

For the purpose of promoting an understanding of the principles of the invention, reference is now to be made to the embodiments illustrates and the specific language would be used to describe the same. It is nevertheless to be understood that no limitations of the scope of the invention is hereby intended, such alterations and further modifications in the illustrated bag and such further applications of the principles of the invention as illustrated therein being contemplated as would normally occur to one skilled in the art to which the invention relates.

The hydro-alcoholic extract of three Ayurvedic plants *Salacia parviflora, Tribulus terrestris* and *Dioscorea glabra* prepared by using 60:40 ratio of water and alcohol respectively is utilized for the development of present novel formulation. In order to establish the beneficial role of test formulation a mechanism based experimental and clinical studies were carried out.

In order to establish the biological activity of single plant candidate as well as combined formulation a mechanism based study was conducted where the role of the drug was validated on cholesterol receptors, pancreatic beta receptor, leptin receptor including pro-inflammatory cytokine inhibitory activity in experimental models. The mode of action of test formulation was proven through its activity on various targets involved with obesity, hypertension, dyslipidemia and insulin resistance as all these four conventional factors are combined at one place called metabolic syndrome.

Further, the therapeutic potentials of test formulation were determined in various pre-clinical and clinical studies. The effect of the test formulation was evaluated on various parameters like leptin and adiponectin (adipokines), IL-6, TNF-α (pro-inflammatory markers), serum insulin, plasminogen activator inhibitor, endothelin-1 and the most important factor is lipids and lipoproteins including apolipo B as all these are associated with metabolic syndrome and responsible for CHD mortality to a great extent.

As reported the increased endothelial permeability is responsible for endothelial dysfunction due to presence of enhanced pro-inflammatory cytokines which is reflected through elevated level of endothelin-1 and IL-8 level.

Before utilizing the drug for human consumption the pre-clinical safety and efficacy profile of single as well as combined formulation were carried out following international norms. The anti-obesity, anti-atherosclerotic and blood glucose lowering activity of test drug was evaluated in experimental models. The animal model of high fat diet induced obesity, high cholesterol diet induced atherosclerosis and streptozotocin induced hyperglycemia for diabetes was designed and beneficial role of test formulation was evaluated on adiponectin, leptin, resistin, blood glucose levels, LDL-c, triglycerides, IL-6, TNF-α and hs CRP in the above experimental models. A mechanism based study indicated the therapeutic potential of the test drug in the prevention and management of metabolic syndrome.

Mechanism Involved in Present Invention:

Till recently, the exact-mechanism or which components of metabolic syndrome are primarily and which are secondary involved with the development of metabolic syndrome is unknown. However, visceral obesity a leads in this syndrome involving angiotensin II receptors, pancreatic beta cells, cholesterol receptors, various adipocytokines releasing from adipose tissues in circulation. Similarly pro-inflammatory state is also associated with obesity responsible for progression of hyperglycemia and cardiovascular involvement.

The molecular and biochemical analysis in metabolic syndrome will provide useful information about the mechanism of action of test substance as regard the prevention and management of metabolic syndrome is concern. For this purpose the assessment of biologically relevant candidate genes in metabolic syndrome through studying the phenotypic traits with specific over expression of selected gene will provide information how to elucidate the specific selected gene candidate in the pathogenesis as well as management of disease condition and also prevent the onset of an adverse cardiac event among of metabolic syndrome patients.

Under this mechanism the mode of action of test formulation inhibits enzymes needed to digest carbohydrates particularly alpha glucosidase and alpha amylase. Inhibition of these enzyme systems reduces the rate of digestion of complex carbohydrates, less glucose is absorbed because carbohydrates are not broken down in glucose molecules. The primary cause of weakened insulin receptor response is the over production of insulin. Studies have indicated that the plant species of *Salacia* containing the active compound salacinol, mangiferin and kotalonol have been found to meet multiple targets in diabetes and obesity through modulating PPAR-α mediated lipogenic gene transcription and AT1 signaling and inhibitory activity of α-glucosidase, aldose reductase and pancreatic lipase. The present test formulation containing the extract of *Dioscorea glabra* and *Salacia parviflora* comprising quantified active molecules have long term effect on weight control through its major biological activity on various adipocytokines and inflammatory cytokines associated with high BMI and waist circumference, resulting in healthy cardiovascular function.

Further, while evaluating the role of test substances present in the plant *Dioscorea glabra* and *Tribulus terrestris* has exerted its effect indicating that this combination checks and reduces the excess accumulation of cardiac lipid and increasing the cardiac fatty acid uptake, thereby modulating cardiac PPAR-γ mediated fatty acid metabolic gene transcription among metabolic syndrome patients. Thus invention in based on mechanism underlying effectiveness of test formulation treatment. similarly the results obtained out of present study also indicated that test formulation inhibited the postprandial hyperglycemia, hyperlipidemia and hepatic steatosis, it activated expression of PPAR-α, mRNA and protein in experimental and clinical investigations and provided the exact mechanism underlying in the effectiveness of test formulation in metabolic syndrome patients.

Thus the mechanism involved with metabolic syndrome indicated improvement in insulin sensitivity along with increase in circulating adiponectin and involved adipocyte responsiveness following treatment with test formulation. It was observed throughout the study that test formulation did not reduce the food intake, it decreases the leptin and enhances adiponectin concentration, proving its anti-obesity, anti-atherosclerotic and anti-inflammatory insulin sensitivity enhancing activity and this beneficial in the management of metabolic syndrome and its adverse complications particularly the cardiovascular events.

Extraction Procedure/Process Adopted in the Present Study:

The extraction solvents aqueous (100% distilled water) and alcohol in the ratio of 60:40 at the temperature of 70 and 90° C., extraction time 6-24 hours was done. The active constituents present in three plants were isolated through HPLC, HPTLC, UV, NMR. The extraction procedure when adopted at 70° C. at a duration of 6 hours, the most efficient and better results were obtained out of the used parts of three plant material. The aqueous with alcohol in a concentration of 70:30 ratio has shown better extraction outcome and we propose this as the better and efficient adjuvant along with highest acceptability by the humans. It is the most effective solvent system (hydro-alcoholic) both in terms of polarity and isolation of bio-active constituents. Under this study we have a novel extraction solvent polarity, temperature and extraction time.

The plant materials (three plants namely *Salacia parviflora*, *Tribulus terrestris* and *Dioscorea glabra*) were collected from Patalkot of Chhindwara Districts, Madhya Pradesh in the month of September, identified by Professional, Botanist. The extracted materials were stored at −80° C., until analysis was carried out.

Steps:
Identification of plant species (DNA Finger printing)
Rationale for selection of plants
A novel extraction procedure
Structural elucidation and spectral analysis by HPLC, GCMS, LCMS-MS & NMR
Purity of the standard
Biotransformation
Biochemical evidence for assessment of efficacy profile
Biochemical and Histopathological changes
Synergistic action
Dose determination
Toxicokinetic profile
Bio-transformation
Physical, biochemical and behavioral changes
Drug to drug and Drug-body interaction (in relation to ethnic group)
Genomic architect of population
Clinical Evidence for efficacy profile The quantitative determinations were done using calibration curves of the active compound and standards, retention times, spectral data and authentic standards.

According to this invention there is provided a plant based Ayurvedic formulation showing efficacy in the prevention and management of metabolic syndrome through its activity on adipokines, pro-inflammatory cytokines, atherogenic dyslipidemic markers, PAI, endothelin-1, adinocine, prostacycline, thromboxanes, prostaglandin E2 etc. The present Ayurvedic test formulation comprising of the following ingredients—

| | |
|---|---|
| 1. *Salacia parviflora* (Saptachakra) | Roots |
| 2. *Tribulus terrestris* (Gokshur) | Fruits |
| 3. *Dioscorea glabra* (Varahikand) | Rhizome (yam) |

Preferably the aforesaid plants are present in the following doses in the test formulation—

| Name of the plants | Dose |
|---|---|
| 1. *Salacia parviflora* | 250-550 mg/day |
| 2. *Tribulus terrestris* | 225-450 mg/day |
| 3. *Dioscorea glabra* | 250-500 mg/day |

The formulation may also comprise known additives such as minerals, vitamins, salts, filler (for capsulation or to prepare syrup) and binders, if required to present in trace amount.

Thus any known additive or supplement is added to prepare the final formulation as required and present in trace amount. Reference is made here in capsule form. However, it would be apparent that the preparation may also be in the form of syrup/tablet.

Preferably but without implying any limitation the present preparation comprises—

| Name of the plants | Dose |
|---|---|
| 1. *Salacia parviflora* | 425 mg/day |
| 2. *Tribulus terrestris* | 200 mg/day |
| 3. *Dioscorea glabra* | 325 mg/day |

Hypothesis:

Metabolic syndrome has a complex etiology and associated with various organ systems. There is strong linkage between insulin resistance, dyslipidemia and endothelial dysfunction. Genetic factor play an important role in the development of CHD. Low grade inflammation is always associated with metabolic syndrome having role in the development of atherosclerosis and hypertension. The linkage between low grade inflammation, dyslipidemia, leads to obesity through alteration of different adipokines. Central regulation of energy production and expenditure is strongly associated with neuro-endocrine network. Therefore, breaking up the linkage may serve as a useful criteria for the development of a new drug entity which targets prevention and management of metabolic syndrome associated dyslidemia, atherosclerosis and type-2 diabetes particularly among genetically prone individuals. The suppression of genes responsible for development of obesity may be targeted by inhibiting leptin metabolism. Therefore, we have selected those plant bio-molecules which inhibits the pro-inflammatory cytokines, formation of triglycerides and apolipo A & B. HDL and adiponectin, the common selected targets responsible for regulation of leptin metabolism.

Alpha glucosidase, amylase and lipid lipase inhibition have also proven our hypothesis that regulation of these parameter may prevent the occurrence of CHD. The plant *Tribulus terrestris* exerted a strong action on the prevention of endothelial dysfunction which is evident from the decrease in pro-inflammatory cytokines, atherogenic dyslipidemia, insulin resistance etc. The novelty of this invention is that for the first time we have selected bio-molecules derived out of three plants which exerted beneficial effects through multi-targeted activity to arrest the functional deterioration of various organs involved with metabolic syndrome.

Sphingosine-1-phosphate is a lipid mediator responsible for activation of inflammation leading to atherosclerosis and thrombogenic events. Sphingosine-1 receptor is located in vascular endothelium. Secretion of IL-6 and IL-8 are generally associated with Sphingosine-1-phosphate receptor gene. Further, it is also regulated by transcriptional factor and Luciferase reporter gene activity. Therefore, Sphingosine-1-phosphate acts as an anti-atherogenic factor. Preservation of vascular integrity can only be maintained by generation of Sphingosine-1-phosphate. Other object is preservation of vascular integrity by regulating pro-inflammatory markers, athrogenic dyslipidemia.

The present plant based Ayurvedic formulation is prepared out of the three plant extracts namely *Salacia parviflora, Tribulus terrestris* and *Dioscorea bulbifera* in effective doses. The formulation has been proven for its activity on leptin metabolism, anti-inflammatory, nitric oxide, PAI, endothelin-1 reducing property. Thus it is proposed that atherogenic dyslipidemia, insulin resistance, altered adipokines and pro-inflammatory markers involved with metabolic syndrome cases can be managed and future risk of coronary heart disease/ischemic heart disease can be prevented by application of present test formulation.

As metabolic syndrome is a multi-factorial disorder and is a major risk factor for coronary heart disease therefore the drugs should not only be targeted to reduce body weight rather it should be equally beneficial in the management of blood pressure, insulin resistance and lipid metabolism. The present test formulation contains the extract of *Salacia parviflora* and *Dioscorea glabra* prominently which has shown anti-obesity, anti-hyperlipidemic and anti-atherosclerotic effect as well as anti-oxidant activity and improvement in insulin resistance in various pre-clinical and clinical studies.

There is substantial hetrogenecity of CVD risk among individuals with increased adiposity. Insulin resistance is found both in obese and lean patients with hypertension. A number of studies indicated that metabolic syndrome results from interplay between several genes and an affluent environment. All components of metabolic syndrome are inherited. The heritability range is 22% to 62% for systolic BP and 38% to 63% for diastolic BP. It is estimated that genetic factors explain approximately 40% of variance in body fat and up to 70% abdominal obesity. Thus genetic factor increases the susceptibility to increase metabolic syndrome, of course also precipitated by environmental factors.

The role of leptin and resistin metabolism may be considered in the development of obesity associated type-2 diabetes mellitus and associated micro-vascular complications and can be used as an early predictor of type-2 diabetes mellitus, where as no other inflammatory and vascular marker can predict onset of diabetes. The modulation of adiponectin is helpful in the prevention and management of type-2 diabetes mellitus and its complications. In our experimental and clinical trials the test formulation revealed that combined formulation has shown effectiveness in the treatment of obesity followed by insulin resistance and atherosclerosis. The cases treated with test formulation revealed lower level of blood glucose, cholesterol, triglyceride, leptin and resistin compared to baseline values. Studies conducted by us, have indicated that dietary diosgenin found in the plant *Dioscorea glabra* has shown lipid lowering, anti-inflammatory and blood glucose lowering effects. The mechanism of action of test drug may be that by regulating the intestinal enzymes there is increase in pancreatic insulin receptor sensitivity and it inhibits these enzymes with the opposite action. In one of the studies conducted by us revealed reduced concentration of leptin and resistin, pro-inflammatory cytokines, apolipo B, PAI and endothelin-1 following test drug treatment exhibiting important anti-obesity, anti-diabetic and anti-atherogenic effects.

Our present invention is based on a new hypothesis which we have proposed to evaluate the therapeutic effect of plant based extracts. It is hypothesized that new formulation regulates the over expression of genes involved with various abnormalities associated with metabolic syndrome. Different peptides and ghrelin regulates the adipocytes and formation of adipokines responsible for dyslipidemia and endothelial dysfunction. Leptin, ghrelin and adiponectin play a vital role in the development of various clinical manifestations like insulin resistance, dyslipidemia, atherosclerosis and ultimately development of coronary heart disease. Our main focus is to target those receptors, linked in transformation of various signaling pathways to minimize the clinical manifestation of obesity, dyslipidemia, insulin resistance and development of CHD.

The low grade inflammation is generally associated with obesity and other abnormalities associated with metabolic syndrome. Therefore, early management of obesity is helpful in reducing the risk of CHD mortality among metabolic syndrome patients.

About the Plants:
1. *Salacia parviflora* (Saptachakra): This plant belongs to Celastraceae including Hippocrataceae family. It is climbing shrub with blackish branches. Root and bark is used for medicinal purposes. It contains sitosterol, mangiferin, catechine, salaciquinane, triterpenoids etc. Mangiferin, salacinol and kotanelol are active constituents of this plant and potent alpha-glucosidase inhibitors that have been shown to decrease serum glucose levels. The active constituent present in the plant also inhibits aldose reductase activity thereby delaying the development of diabetic complications like diabetic neuropathy and nephropathy. It also has anti-obesity, anti-inflammatory role.
2. *Tribulus terrestris* (Gokshur): belongs to zygophyllaceae family. It is found throughout India up to 11,000 ft. The active constituents is Diosgenin, gitogenin, chlorogenin, kaempferol, 3-glucoside, 3-rutinoside and tribuloside isolated from fruit and leaves of *Tribulus terrestris*. There are some of other constituents like alkaloids, β-sitosterol etc. found in this plant. The plant *Tribulus terrestris* is one of the ingredients of present test formulation used for the treatment of arterial blood pressure and has cardiac stimulant action.
3. *Dioscorea glabra* (Varahikand): It is a member of the Dioscoraceae family. Tubers of *Dioscorea* have been used throughout the world as a food and herbal medicine. The pharmacologically active major component of the *Dioscorea glabra* is diosgenin, which is a steroidal saponin and dioscin, a form of diosgenin with sugars attached. One of the recent studies conducted by us suggested that dietary diosgenin may lower triglyceride levels, reduce blood sugar and decreases vascular inflammation. The phyto-steroids have been shown to lower plasma cholesterol levels. Dietary diosgenin has also shown decrease in plasma cholesterol and decrease in cholesterol absorption, liver cholesterol levels. In addition diosgenin improved cholesterol absorption through reducing lipid lipase and amylase levels.

Rationale for selection of plants:
1. *Salacia parviflora*—It contains the active constituent mangiferin, salacinol and kotanelol in a specific concentration. The active constituents are mainly mangiferin and salacinol, not influence the intestinal enzyme, rather acts on pancreatic beta cells and activate to secrete more insulin. It also acts as PPAR-α and γ agonist, thus regulates the lipid lipoprotein metabolism particularly apolipo(a) and B. In other words it prevents the insulin resistance, enhance the insulin sensitivity with there property this plant was selected to prepare the novel formulation.
2. *Diascorea glabra*—It contains isobulbinoside along with diosgenin, therefore its main action is on the adipokines, reduces pro-inflammatory cytokines IL-6, IL-10 including CRP, regulates leptin metabolism, enhances adiponectin and reduces body fat. It prevents the endothelial dysfunction by reducing endothelin-1 and plasminogen activator inhibitor.
3. *Tribulus terrestris*—It contains mainly disogenin, and tribuloside isolated from the fruits showing its activity as blood pressure lowering and cardiac stimulant activity. It reduces inflammatory process. Saponins namely terrestrosins A, B, C, D and E, desgalactotigonis, F-gitonis, desglucolanatigoneis, gitnin etc., which on hydrolysis yield diosgenis, hecogenis and neotigogenin etc. are the active constituents showing blood pressure lowering activity along with prevention from atherosclerosis process through reducing inflammatory process.

There are other minor constituents like alkaloids (uncharacterised), common phyto sterols namely, □-sitosterol, stigmasterol, a cinnamic amide derivative—terrestiamide and 7-methylhydroisdamone.

*Salacia parviflora* and *Dioscorea glabra* when given along with *Tribulus terrestris* in combined form it enhances the potentiality of both *Salacia parviflora* and *Dioscorea glabra* proven through various parameters involved with metabolic syndrome. Steroidal saponin namely terresttrosins A, B, C, D, and E it reduces PAI and tPAI and also reduces endothelin-1 thus prevents the damage of endothelium and ultimately reducing the CHD mortality risk.

The presence of active constituents prevents the further progression of atherosclerosis, regulates the abnormal lipids, enhances the insulin sensitivity and also regulates the leptin metabolism. Thus prevents obesity related complications including pro-inflammatory cytokines. This novel formulation has a inventive step and acts on various receptor regulates various biochemical parameters involved with metabolic syndrome.

Example-I

When the Hydro-alcoholic extract of *Salacia parviflora* in the dose of 100 mg/kg/day, *Dioscorea glabra* in the dose of 75 mg/kg/day and *Tribulus terrestris* 75 mg/kg/day mixed and given to high fructose diet induced metabolic syndrome regulated the leptin metabolism and improved insulin sensitivity, reduced blood glucose level through acting on pancreatic beta cells.

Example-II

When the hydro-alcoholic extract of *Dioscorea glabra* in the dose of 150 mg/kg/day, *Tribulus terrestris* in the dose of 150 mg/kg/day was mixed and given to high fructose diet induced obese animals decrease in leptin, increase in adiponectin and regulation of atherogenic dyslipidemia was noticed as the triglyceride level decreased and HDL-c increased after treatment.

Example-III

When the hydro-alcoholic extract of *Dioscorea glabra* in the dose of 325 mg/day, and *Salacia parviflora* in the dose of 375 mg/day mixed and orally administered to diagnosed metabolic syndrome patients decrease in glycosyalted hemoglobin and postprandial blood glucose level to 40 percent was estimated. Further, the inflammatory cytokines TNF-α, IL-6 along with hs-CRP also decreased after treatment. Thus the atherosclerotic process checked and improved significantly in metabolic syndrome cases.

Example-IV

When the hydro-alcoholic extract of *Dioscorea glabra* 450 mg/day and *Tribulus terrestris* 375 mg/day mixed and given to metabolic syndrome patients, decrease in blood pressure and apolipo B level was observed which modified atherosclerotic process indicated the prevention from CHD mortality and morbidity among metabolic patients.

Example-V

When the hydro-alcoholic extract of *Salacia parviflora* in the dose of 375 mg/day, *Dioscorea glabra* in the dose of 250 mg/day and *Tribulus terrestris* in the dose of 250 mg/day mixed and given to metabolic syndrome patients, reduced leptin, resistin, hsCRP including plasminogen activator inhibitor, endothelin-1 and thus beneficial in the prevention and management of endothelial dysfunction among metabolic syndrome patients.

Example-VI

When the extract of *Dioscorea glabra* in the dose of 425 mg/day, *Salacia parviflora* in the dose of 375 mg/day was combined and given to patients of metabolic syndrome, maintains the vascular tone through endothelial derived relaxing factor like adinocine, prostacycline, thromboxanes and prostaglandin E2 resulting in reduced risk of vasoconstriction.

Example-VII

When the hydro-alcoholic extract of *Dioscorea glabra* in the dose of 325 mg/day, *Salacia parviflora* in the dose of 425 mg/day and *Tribulus terrestris* in the dose of 200 mg/day mixed and given to metabolic syndrome patients, inhibited the pancreatic lipase enzyme with the result reduction in blood glucose level, modification in abnormal lipids including decrease of altered adipokine and resistin, leptin and inflammatory markers TNF-α, IL-6 and hs CRP was recorded. This combination of test formulation prevented the endothelial dysfunction by showing its activity as anti-inflammatory, anti-obesity, anti-atherosclerotic. As synergism when the *Tribulus terrestris* is added with *Salacia parviflora* and *Dioscorea glabra* it potentiated the action of the drug through its activity as anti-oxidant (reduced nitric oxide) and immunopotentiator. On the whole the test formulation has anti-obesity, anti-hyperlipidemic, anti-inflammatory role with potential to improve insulin sensitivity.

Example-VIII

When the organic extract of *Tribulus terrestris* in the dose of 350 mg/day and *Dioscorea glabra* in the dose of 475 mg/day mixed and given the metabolic syndrome patients enhanced the insulin sensitivity, improved glucose metabolism and altered lipid levels in metabolic syndrome patients.

The non-clinical and clinical safety profile assessment indicated that the drug is safe and can be given for longer time without any adverse reaction.

Experimental Pharmacology of Test Formulation

Efficacy Profile of Test Formulation Evaluated Through Experimentally Designed Model of Metabolic Syndrome—(Fructose Enriched Diet Model)

In this experimental study the Sprague dowely rats (SDR) were selected. Study was divided into three groups—
Group-I: Normal chow diet (N=6)
Group-II: Fructose enriched diet (N=6)
Group-III: Fructose enriched diet+Test formulation (250 mg/kg b.w.) for a period of 30th days (N=6)
(Harlan Teklad, Madison Wis.)

| Composition of High Fructose Diet | Normal Chow Diet composition |
|---|---|
| Fructose - 60% | Starch - 50% |
| Protein - 21% | Protein - 21% |
| Fat - 5% | Fat - 4% |
| Cellulose - 8% | Cellulose - 4.5% |

Both the diet contains standard vitamins, and mineral mix.

The experiment was conducted according to the guidelines for Animal Care and Treatment of the Institute Ethics Committee.

18 Male SDRs weighing 190±25 g were selected and maintained at the temperature controlled room 22° C. and kept on a 14/10 h light dark cycle, food and water were available ad libitum.

Parameters:

Triglycerides, Serum insulin, Total cholesterol, glucose tolerance, systolic blood pressure.

The tests were performed at baseline (before treatment) and at the 30th day of completion of experiment.

Method:

The systolic blood pressure was measured in rats using the fail cutt technique (Narco Biosystems, Houston, Tex.). The rats were acclimatized at 37° C. for 30 minutes before measurement of blood pressure. The blood samples were collected from the retro-orbital sinus under low grade anesthesia of 5 h of fasting. The plasma was reported stored frozen until tested. Plasma insulin was estimated using RIA kit. Triglycerides and Total cholesterol level were measured by an automated analyzer of an enzymatic colorimetric reaction technique, glucose tolerance was tested using oral glucose tolerance test. Fasting blood glucose was measured using standard glucometer, for glucose tolerance test. 3.5 g glucose was administered orally (gastric gavage) just after fasting blood glucose test at 30, 60 and 1.20 minutes of glucose intake. The tests were performed at initial (before treatment) after 15 days and after 30 days of administration of test formulation.

TABLE 1

Pattern of various parameters associated with metabolic syndrome (experimental study)

| Groups | | Total body weight (g) | Systolic BP (mmHg) | Total cholesterol (mg/dl) | Triglycerides (mg/dl) | Plasma insulin (µg/ml) |
|---|---|---|---|---|---|---|
| Normal control | Normal chow diet (N = 6)* | 138.91 ± 19.45 | 118.63 ± 3.75 | 96.42 ± 12.32 | 109.42 ± 9.72 | 21.55 ± 5.97 |
| High Fructose diet (HFD) | Disease control group (N = 6)** | 145.64 ± 20.91 | 124.90 ± 4.04 | 90.35 ± 11.45 | 101.83 ± 8.45 | 22.86 ± 6.01 |
| HFD + Test formulation (250 mg/kg/day) | Treated group (N = 6)*** | 134.93 ± 18.64 | 121.83 ± 3.94 | 92.42 ± 10.93 | 99.62 ± 10.03 | 22.79 ± 5.88 |
| HFD + Test formulation (500 mg/kg/day) | Treated group (N = 6)**** | 151.82 ± 19.11 | 120.64 ± 3.85 | 93.86 ± 11.68 | 97.35 ± 8.60 | 20.62 ± 4.90 |
| Comp. * vs** | | $P > 0.05$ | $P > 0.05$ | $P > 0.05$ | $P < 0.001$ | $P > 0.05$ |
| * vs *** | | $P > 0.05$ | $P > 0.05$ | $P > 0.05$ | $P > 0.05$ | $P > 0.05$ |
| * vs **** | | $P > 0.05$ | $P > 0.05$ | $P > 0.05$ | $P > 0.05$ | $P > 0.05$ |
| ** vs *** | | $P > 0.05$ | $P > 0.05$ | $P > 0.05$ | $P > 0.05$ | $P > 0.05$ |
| ** vs **** | | $P > 0.05$ | $P > 0.05$ | $P > 0.05$ | $P > 0.05$ | $P > 0.05$ |

TABLE 2

Effect of test formulation on metabolic markers in experimental study of metabolic syndrome. (After 15 days treatment)

| Groups | | Total body weight (g) | Systolic BP (mmHg) | Total cholesterol (mg/dl) | Triglycerides (mg/dl) | Plasma insulin (µg/ml) |
|---|---|---|---|---|---|---|
| Normal control | Normal chow diet (N = 6)* | 103.72 ± 20.40 | 116.90 ± 5.02 | 94.10 ± 6.22 | 98.64 ± 17.01 | 22.04 ± 4.87 |
| High Fructose diet (HFD) | Disease control group (N = 6)** | 97.66 ± 18.22 | 131.62 ± 6.32 | 101.45 ± 4.13 | 194.73 ± 43.85 | 31.64 ± 3.90 |
| HFD + Test formulation (250 mg/kg/day) | Treated group (N = 6)*** | 81.20 ± 12.45 | 121.45 ± 4.90 | 95.12 ± 6.45 | 167.94 ± 36.90 | 26.42 ± 3.14 |
| HFD + Test formulation (500 mg/kg/day) | Treated group (N = 6)**** | 76.09 ± 11.75 | 123.84 ± 5.31 | 96.78 ± 7.11 | 158.63 ± 33.75 | 25.36 ± 5.02 |
| Comp. * vs** | | $P > 0.05$ | $P < 0.01$ | $P > 0.05$ | $P < 0.01$ | $P < 0.01$ |
| * vs *** | | $P > 0.05$ | $P > 0.05$ | $P > 0.05$ | $P < 0.01$ | $P > 0.05$ |
| * vs **** | | $P < 0.05$ | $P > 0.05$ | $P > 0.05$ | $P < 0.01$ | $P > 0.05$ |
| ** vs *** | | $P > 0.05$ | $P > 0.05$ | $P > 0.05$ | $P > 0.05$ | $P > 0.05$ |
| ** vs **** | | $P > 0.05$ | $P > 0.05$ | $P > 0.05$ | $P > 0.05$ | $P > 0.05$ |

TABLE 3

Effect of test formulation on various markers after 30 days in experimental metabolic syndrome animal model

| Groups | | Total body weight (g) | Systolic BP (mmHg) | Total cholesterol (mg/dl) | Triglycerides (mg/dl) | Plasma insulin (µg/ml) |
|---|---|---|---|---|---|---|
| Normal control | Normal chow diet (N = 6)* | 113.42 ± 15.82 | 121.94 ± 5.42 | 97.94 ± 8.12 | 97.32 ± 20.42 | 21.64 ± 3.42 |
| High Fructose diet (HFD) | Disease control group (N = 6) ** | 109.25 ± 13.98 | 143.64 ± 6.11 | 106.42 ± 7.90 | 288.42 ± 95.68 | 43.90 ± 5.11 |
| HFD + Test formulation (250 mg/kg/day) | Treated group (N = 6) *** | 89.38 ± 12.42 | 132.90 ± 4.87 | 98.22 ± 4.97 | 193.45 ± 71.32 | 30.42 ± 4.85 |
| HFD + Test formulation (500 mg/kg/day) | Treated group (N = 6) **** | 88.45 ± 10.86 | 130.66 ± 4.95 | 97.35 ± 5.11 | 187.94 ± 66.45 | 29.60 ± 4.16 |
| Comp. * vs** | | $P > 0.05$ | $P < 0.001$ | $P > 0.05$ | $P < 0.01$ | $P < 0.001$ |
| * vs *** | | $P < 0.05$ | $P < 0.05$ | $P > 0.05$ | $P < 0.05$ | $P < 0.01$ |
| * vs **** | | $P < 0.05$ | $P > 0.05$ | $P < 0.05$ | $P < 0.05$ | $P < 0.01$ |
| ** vs *** | | $P < 0.05$ | $P > 0.05$ | $P > 0.05$ | $P > 0.05$ | $P < 0.01$ |
| ** vs **** | | $P < 0.05$ | $P < 0.01$ | $P > 0.05$ | $P > 0.05$ | $P < 0.01$ |

TABLE 4

Glucose tolerance test following 15 days and 30 days test formulation treatment.

| Groups | | After 15 days | | | | After 30 days | | | |
|---|---|---|---|---|---|---|---|---|---|
| | | 0 min | 50 min | 100 min | 150 min | 0 min | 50 min | 100 min | 150 min |
| Normal control | Normal chow diet (N = 6)* | 78.10 ± 7.04 | 71.35 ± 10.42 | — | 73.86 ± 5.09 | — | 75.82 ± 6.32 | 68.22 ± 8.01 | 79.32 ± 6.90 |
| High Fructose diet (HFD) | Disease control group (N = 6) ** | 79.45 ± 6.35 | 188.42 ± 44.10 | 160.45 ± 17.23 | 136.82 ± 16.28 | 124.40 ± 8.25 | 196.70 ± 25.92 | 174.22 ± 21.64 | 148.30 ± 13.45 |
| HFD + Test formulation (250 mg/kg/day) | Treated group (N = 6) *** | 83.42 ± 7.32 | 153.94 ± 39.62 | 133.52 ± 15.2 | 112.36 ± 11.20 | 107.98 ± 20.42 | 141.38 ± 19.90 | 119.35 ± 16.45 | 98.42 ± 7.25 |
| HFD + Test formulation (500 mg/kg/day) | Treated group (N = 6) **** | 87.10 ± 6.93 | 147.44 ± 30.18 | 129.73 ± 16.13 | 108.94 ± 9.75 | 105.22 ± 9.68 | 135.65 ± 8.90 | 106.35 ± 9.64 | 93.82 ± 8.33 |
| Comp. * vs** | | $P > 0.05$ | $P < 0.001$ | $P < 0.001$ | $P < 0.001$ | $P < 0.001$ | $P < 0.001$ | $P < 0.001$ | $P < 0.001$ |
| * vs *** | | $P > 0.05$ | $P < 0.001$ | $P < 0.001$ | $P < 0.001$ | $P < 0.001$ | $P < 0.05$ | $P < 0.01$ | $P < 0.01$ |
| * vs **** | | $P < 0.05$ | $P < 0.001$ | $P < 0.001$ | $P < 0.001$ | $P < 0.001$ | $P < 0.01$ | $P < 0.001$ | $P > 0.05$ |
| ** vs *** | | $P > 0.05$ | $P > 0.05$ | $P < 0.05$ | $P < 0.05$ | $P < 0.01$ | $P > 0.05$ | $P < 0.01$ | $P < 0.001$ |
| ** vs **** | | $P > 0.05$ | $P > 0.05$ | $P < 0.05$ | $P < 0.05$ | $P < 0.05$ | $P < 0.05$ | $P < 0.001$ | $P > 0.05$ |

Results:

The administration of high fructose diet to rats exhibited marked increase in parameters under investigation like total cholesterol, triglycerides, plasma insulin. In addition the high fructose-fed rats showed impaired glucose tolerance following standard oral glucose administration (Table-1-4). Table showed no such significant changes in parameters of control group where normal chow diet was given.

A similar weight gain was noticed in both control group, disease control and test formulation treated group. However, the weight gain in test formulation treated group is comparative less in comparison to disease control group. The test formulation has shown anti-hyperlipidemic, anti-atherosclerotic, insulin sensitivity enhancing property and body weight controlling activity.

It is concluded that the fructose-fed rats represented environmentally acquired metabolic syndrome and the role of test formulation exerted beneficial role in the management of various aspects of metabolic syndrome thus proposed to be beneficial for human metabolic syndrome components.

Study-II

In another experimental study the effect of test formulation was evaluated on lipid and lipoprotein cholesterol among animal model of high cholesterol diet induced hypercholesterolemia, Dose –250 mg/kg b.w.

TABLE 1

Role of test formulation on Total cholesterol among high cholesterol diet treated rats

| | Total cholesterol level (mg/dl) | | |
|---|---|---|---|
| Groups | Initial | after 15 day | after 1 month |
| Normal control (N = 10)* | 64.32 ± 7.89 | 63.80 ± 6.52 | 64.70 ± 8.42 |
| High cholesterol diet (N = 10)** | — | 895.42 ± 49.75 | 480.82 ± 40.72 |

TABLE 1-continued

Role of test formulation on Total cholesterol among high cholesterol diet treated rats

| Groups | Total cholesterol level (mg/dl) | | |
|---|---|---|---|
| | Initial | after 15 day | after 1 month |
| High cholesterol diet + test formulation 250 mg/kg b.w. (N = 10)*** | — | 738.44 ± 90.85 | 378.50 ± 38.20 |
| High cholesterol diet + statin (2.5 mg/kg/day) (N = 10)**** Comparison | — | 691.52 ± 78.85 | 280.50 ± 16.80 |
| * vs** | $P > 0.05$ | $P < 0.001$ | $P < 0.001$ |
| ** vs*** | | $P < 0.001$ | $P < 0.001$ |
| ***vs **** | | $P < 0.001$ | $P < 0.001$ |

TABLE 2

Effect of test formulation on HDL-c level among high cholesterol diet treated rats

| Groups | HDL-c level (mg/dl) | | |
|---|---|---|---|
| | Initial | after 15 day | after 1 month |
| Normal control (N = 10)* | 22.50 ± 4.33 | 23.32 ± 2.85 | 22.37 ± 3.85 |
| High cholesterol diet (N = 10)** | — | 17.82 ± 5.32 | 13.85 ± 1.85 |
| High cholesterol diet + test formulation 250 mg/kg b.w. (N = 10)*** | — | 19.60 ± 3.85 | 21.20 ± 3.85 |
| High cholesterol diet + Statin (2.5 mg/kg/day) (N = 10)**** Comparison | — | 20.32 ± 4.85 | 21.85 ± 3.85 |
| * vs** | $P > 0.05$ | $P < 0.05$ | $P < 0.001$ |
| ** vs*** | | $P > 0.05$ | $P < 0.001$ |
| ***vs **** | | $P > 0.05$ | $P < 0.05$ |

TABLE 3

Effect of test formulation on LDL-c level among high cholesterol diet treated rats

| Groups | LDL-c level (mg/dl) | | |
|---|---|---|---|
| | Initial | after 15 day | after 1 month |
| Normal control (N = 10)* | 23.85 ± 4.78 | 22.75 ± 5.72 | 24.22 ± 6.85 |
| High cholesterol diet (N = 10)** | — | 341.50 ± 62.32 | 314.40 ± 48.34 |
| High cholesterol diet + test formulation 250 mg/kg b.w. (N = 10)*** | — | 274.50 ± 41.93 | 142.55 ± 32.08 |
| High cholesterol diet + Statin (2.5 mg/kg/day) (N = 10)**** Comparison | — | 255.80 ± 37.38 | 108.85 ± 16.85 |
| * vs** | $P > 0.05$ | $P < 0.001$ | $P < 0.001$ |
| ** vs*** | | $P < 0.05$ | $P < 0.001$ |
| ***vs **** | | $P > 0.05$ | $P < 0.05$ |

TABLE 4

Effect of test formulation on Triglycerides level among high cholesterol diet treated rats

| Groups | Triglycerides level (mg/dl) | | |
|---|---|---|---|
| | Initial | after 15 day | after 1 month |
| Normal control (N = 10)* | 26.85 ± 8.70 | 30.32 ± 7.85 | 28.40 ± 5.52 |
| High cholesterol diet (N = 10)** | — | 340.70 ± 64.80 | 298.50 ± 39.32 |
| High cholesterol diet + Test formulation (N = 10)*** | — | 260.55 ± 69.85 | 174.93 ± 21.78 |
| High cholesterol diet + Statin (2.5 mg/kg/day) (N = 10)**** Comparison | — | 228.50 ± 31.80 | 112.85 ± 19.30 |
| * vs** | $P > 0.05$ | $P < 0.001$ | $P < 0.001$ |
| ** vs*** | | $P < 0.05$ | $P < 0.01$ |
| ***vs **** | | $P > 0.05$ | $P < 0.05$ |

Clinical Study:

Material & Methods:

The study population consisted of 128 diagnosed Metabolic Syndrome cases (76 Men and 52 Women), aged 52.81±9.68 years at study entry. The cases were diagnosed as per criteria given by WHO for classification and diagnosis of Metabolic Syndrome.

Selection Criteria

| Waist circumference 100 cm | (>40" inches chest for men) |
| | (>35" inches chest for women) |
| Blood pressure | >130 mmHg systolic |
| | >85 mmHg diastolic |
| Fasting glucose | >100 mg/dl |
| Triglycerides | >150 mg/dl |
| HDL | <40 mg/dl for men and <50 mg/dl for women |

After preliminary screening the subjects showing association with 3 or more than 3 above factors were selected. The clinical trial was conducted in three groups—

Group-I:

36 cases were treated with Orlistat (120 mg twice a day after each meals).

Group-II:

44 cases were treated with Ayurvedic formulation.

Group-III:

48 cases were administered Orlistat along with Ayurvedic formulation.

Method:

Body mass index (BMI) was calculated following formula {weight (kg)÷ height (m2)} and anthropometer was used for circumference measurement. Lipid profile including triglyceride was estimated by standard laboratory kits. TNF-□, interleukin-6 was measured by ELISA kit, adiponectin by radioimmunoassay kit. CRP by kit for quantitative nephelometric determination of CRP in human serum or plasma by Turbox/Turbox analyzer and ELISA activity assay kit for Leptin level. Subjects suffering from any other disease known to affect the study parameters were excluded from the series. Upon recruitment all subjects gave informed written consent.

TABLE 1

Reduction in Body Mass Index following test drug treatment in Metabolic Syndrome cases.

| Treatment groups | Sex | No. of cases | Body Mass Index (BMI) Initial | After 3 months | After 6 months | Comp. Initial vs After 6 months |
|---|---|---|---|---|---|---|
| Conventional drug treatment | Male | 21 | 31.02 ± 2.16 | 29.46 ± 2.00 | 29.13 ± 1.69 | P < 0.001 |
| | Female | 15 | 32.26 ± 2.06 | 30.35 ± 2.14 | 28.85 ± 2.03 | P < 0.001 |
| Test formulation treatment | Male | 28 | 30.75 ± 3.02 | 28.81 ± 2.73 | 27.82 ± 2.04 | P < 0.001 |
| | Female | 16 | 31.85 ± 2.65 | 29.71 ± 2.23 | 28.87 ± 2.61 | P < 0.001 |
| Conventional drug + test formulation treatment | Male | 27 | 31.85 ± 3.01 | 28.55 ± 3.02 | 26.89 ± 2.14 | P < 0.001 |
| | Female | 21 | 32.61 ± 2.44 | 29.86 ± 2.36 | 28.29 ± 3.02 | P < 0.001 |
| Normal range: | | | | | 18-24 | |

TABLE 2

Beneficial effect of test formulation on blood pressure in Metabolic Syndrome cases

| Treatment groups | No. of cases | Systolic blood pressure (mmHg) Initial | After 6 months | Comp. Initial vs After 6 months | Diastolic blood pressure (mmHg) Initial | After 6 months | Comp. Initial vs After 6 months |
|---|---|---|---|---|---|---|---|
| Conventional drug treatment | 36 | 136.68 ± 9.02 | 124.87 ± 8.11 | P < 0.001 | 89.04 ± 4.22 | 86.24 ± 4.04 | P < 0.001 |
| Test formulation treatment | 44 | 134.90 ± 11.62 | 127.35 ± 7.90 | P < 0.001 | 88.90 ± 4.38 | 84.40 ± 2.11 | P < 0.001 |
| Conventional drug + test formulation treatment | 48 | 140.32 ± 9.22 | 123.42 ± 6.90 | P < 0.001 | 90.04 ± 3.97 | 83.11 ± 3.02 | P < 0.001 |

TABLE 3

Decrease in blood glucose levels following test drug treatment in Metabolic Syndrome cases

| Treatment groups | No. of cases | Fasting blood glucose (mg/dl) Initial | After 6 months | Comp. Initial vs After 6 months | Postprandial blood glucose (mg/dl) Initial | After 6 months | Comp. Initial vs After 6 months |
|---|---|---|---|---|---|---|---|
| Conventional drug treatment | 36 | 136.42 ± 7.08 | 108.42 ± 7.93 | P < 0.001 | 231.68 ± 24.90 | 179.45 ± 18.36 | P < 0.001 |
| Test formulation treatment | 44 | 135.85 ± 8.45 | 118.42 ± 8.72 | P < 0.001 | 229.45 ± 21.68 | 175.93 ± 12.42 | P < 0.001 |
| Conventional drug + test formulation treatment | 48 | 138.97 ± 9.86 | 91.82 ± 5.74 | P < 0.001 | 294.02 ± 28.24 | 162.79 ± 13.45 | P < 0.001 |

TABLE 4

Decline in total cholesterol and triglycerides concentration
following test drug treatment in Metabolic Syndrome cases.

| Treatment groups | No. of cases | Total cholesterol (mg/dl) | | Comp. Initial vs After 6 months | Triglycerides (mg/dl) | | Comp. Initial vs After 6 months |
| --- | --- | --- | --- | --- | --- | --- | --- |
| | | Initial | After 6 months | | Initial | After 6 months | |
| Conventional drug treatment | 36 | 247.90 ± 28.82 | 216.92 ± 31.42 | P < 0.001 | 354.86 ± 63.03 | 287.93 ± 58.11 | P < 0.001 |
| Test formulation treatment | 44 | 238.87 ± 31.62 | 208.92 ± 37.46 | P < 0.001 | 311.08 ± 47.42 | 270.94 ± 51.70 | P < 0.001 |
| Conventional drug + test formulation treatment | 48 | 239.78 ± 41.64 | 182.04 ± 31.82 | P < 0.001 | 348.90 ± 61.84 | 251.82 ± 48.90 | P < 0.001 |
| Normal range: | | 150-200 (mg/dl) | | | ≤150 (mg/dl) | | |

TABLE 5

Improvement in insulin sensitivity under
influence of test formulation.

| Treatment groups | No. of cases | HbA1c (%) | | | Comp. Initial vs After 6 months |
| --- | --- | --- | --- | --- | --- |
| | | Initial | After 3 months | After 6 months | |
| Conventional drug treatment | 36 | 6.82 ± 1.22 | 5.93 ± 0.86 | 5.24 ± 1.20 | P < 0.05 |
| Test formulation treatment | 44 | 6.94 ± 1.36 | 5.75 ± 1.13 | 5.21 ± 0.88 | P < 0.001 |
| Conventional drug + test formulation treatment | 48 | 7.04 ± 1.42 | 6.08 ± 1.88 | 5.37 ± 1.04 | P < 0.001 |
| Normal range: | | 18-24 | | | |

TABLE 6

Beneficial role of test drug on LDL-c and HDl-c among Metabolic Syndrome cases.

| Treatment groups | No. of cases | LDL-c (mg/dl) | | Comp. Initial vs After 6 months | HDL-c (mg/dl) | | Comp. Initial vs After 6 months |
| --- | --- | --- | --- | --- | --- | --- | --- |
| | | Initial | After 6 months | | Initial | After 6 months | |
| Conventional drug treatment | 36 | 139.72 ± 9.88 | 114.32 ± 8.04 | P < 0.001 | 41.62 ± 4.02 | 43.02 ± 3.11 | P < 0.001 |
| Test formulation treatment | 44 | 141.02 ± 39.45 | 121.49 ± 41.02 | P < 0.001 | 39.88 ± 5.13 | 44.01 ± 2.77 | P < 0.001 |
| Conventional drug + test formulation treatment | 48 | 142.85 ± 27.20 | 107.32 ± 24.64 | P < 0.001 | 42.89 ± 3.90 | 46.04 ± 3.16 | P < 0.001 |
| Normal range: | | ≤100 (mg/dl) | | | ≥45 (mg/dl) | | |

TABLE 7

Beneficial role of test drug on apolipo (B) among Metabolic Syndrome cases.

| Treatment groups | No. of cases | Apolipo (B) (mg/dl) Initial | Apolipo (B) (mg/dl) After 6 months | Comp. Initial vs After 6 months |
|---|---|---|---|---|
| Conventional drug treatment | 36 | 188.73 ± 32.80 | 152.87 ± 18.91 | P < 0.001 |
| Test formulation treatment | 44 | 193.84 ± 41.62 | 148.45 ± 37.42 | P < 0.001 |
| Conventional drug + test formulation treatment | 48 | 197.34 ± 38.72 | 129.46 ± 30.62 | P < 0.001 |
| Normal range: | | 55-159 (mg/dl) | | |

TABLE 8

Regulation of pro-inflammatory cytokines following test drug treatment in Metabolic Syndrome cases

| Treatment groups | No. of cases | hs CRP (mg/L) Initial | hs CRP (mg/L) After 6 months | Comp. Initial vs After 6 months | Interleukin-6 (pg/ml) Initial | Interleukin-6 (pg/ml) After 6 months | Comp. Initial vs After 6 months |
|---|---|---|---|---|---|---|---|
| Conventional drug treatment | 36 | 4.93 ± 0.82 | 3.64 ± 0.75 | P < 0.001 | 2.25 ± 0.16 | 2.12 ± 0.29 | P < 0.05 |
| Test formulation treatment | 44 | 5.09 ± 1.06 | 3.62 ± 1.04 | P < 0.001 | 1.87 ± 0.28 | 1.25 ± 0.30 | P < 0.001 |
| Conventional drug + test formulation treatment | 48 | 4.97 ± 0.64 | 3.09 ± 0.82 | P < 0.001 | 1.97 ± 0.29 | 0.85 ± 0.16 | P < 0.05 |
| Normal range: | | 1-3 (mg/L) | | | <1 (pg/ml) | | |

TABLE 9

Decrease in TNF-α and Endothelin concentration following test drug treatment in Metabolic Syndrome cases

| Treatment groups | No. of cases | TNF-α (pg/ml) Initial | TNF-α (pg/ml) After 6 months | Comp. Initial vs After 6 months | Endothelin (pg/ml) Initial | Endothelin (pg/ml) After 6 months | Comp. Initial vs After 6 months |
|---|---|---|---|---|---|---|---|
| Conventional drug treatment | 36 | 622.45 ± 65.35 | 488.90 ± 122.45 | P < 0.001 | 1286.93 ± 304.42 | 988.73 ± 101.28 | P < 0.001 |
| Test formulation treatment | 44 | 639.75 ± 71.28 | 470.88 ± 116.36 | P < 0.001 | 1294.86 ± 280.72 | 886.83 ± 112.73 | P < 0.001 |
| Conventional drug + test formulation treatment | 48 | 592.45 ± 82.78 | 439.22 ± 116.68 | P < 0.001 | 1175.77 ± 204.83 | 728.45 ± 86.28 | P < 0.001 |
| Normal range: | | 25-800 (pg/ml) | | | 0.32-1000 pg/ml | | |

TABLE 10

Effect of test drug on Leptin and Adiponectin concentration in Metabolic Syndrome cases

| Treatment groups | No. of cases | Leptin (µg/L) Initial | After 6 months | Comp. Initial vs After 6 months | Adiponectin (µg/ml) Initial | After 6 months | Comp. Initial vs After 6 months |
|---|---|---|---|---|---|---|---|
| Conventional drug treatment | 36 | 36.42 ± 4.01 | 25.73 ± 3.98 | P < 0.001 | 6.92 ± 1.44 | 7.39 ± 2.19 | P < 0.001 |
| Test formulation treatment | 44 | 38.11 ± 4.09 | 27.22 ± 3.80 | P < 0.001 | 6.85 ± 1.36 | 10.11 ± 2.73 | P < 0.001 |
| Conventional drug + test formulation treatment | 48 | 39.82 ± 5.16 | 22.84 ± 4.04 | P < 0.001 | 5.86 ± 1.29 | 11.68 ± 2.75 | P < 0.001 |
| Normal range: | | 5-12 (µg/L) | | | 5-30 (µg/mL) | | |

TABLE 11

Effect of test formulation on Plasminogen Activator Inhibitor (PAI-1) in metabolic syndrome cases

| Treatment groups | No. of cases | PAI-1 (ng/ml) Initial | After 3 months | After 6 months | Comp. Initial vs After 6 months |
|---|---|---|---|---|---|
| Conventional drug treatment | 36 | 40.12 ± 5.16 | 37.42 ± 4.95 | 32.98 ± 4.65 | P < 0.001 |
| Test formulation treatment | 44 | 39.25 ± 6.01 | 32.91 ± 4.73 | 30.88 ± 3.97 | P < 0.001 |
| Conventional drug + test formulation treatment | 48 | 42.10 ± 7.98 | 31.97 ± 5.13 | 27.11 ± 4.25 | P < 0.001 |

TABLE 12

Decrease in Plasminogen Activator (tPA-1) following test formulation treatment in metabolic syndrome patients

| Treatment groups | No. of cases | tPA-1 (ng/ml) Initial | After 3 months | After 6 months | Comp. Initial vs After 6 months |
|---|---|---|---|---|---|
| Conventional drug treatment | 36 | 21.23 ± 3.28 | 19.45 ± 3.01 | 18.46 ± 3.10 | P > 0.05 |
| Test formulation treatment | 44 | 22.01 ± 3.97 | 18.42 ± 2.99 | 17.29 ± 3.04 | P < 0.05 |
| Conventional drug + test formulation treatment | 48 | 22.98 ± 5.16 | 17.21 ± 4.06 | 15.85 ± 2.75 | P < 0.001 |

TABLE 13

Amelioration in CD36 concentration following test formulation treatment in metabolic syndrome patients

| Treatment groups | Gender | No. of cases | CD36 (ng/mL) Initial | After 3 months | After 6 months | Comp. Initial vs After 6 months |
|---|---|---|---|---|---|---|
| Conventional drug treatment | M | 15 | 188.62 ± 31.24 | 173.64 ± 24.48 | 196.22 ± 39.68 | P > 0.05 |
| | F | 10 | 142.90 ± 40.29 | 156.42 ± 38.56 | 155.90 ± 37.86 | P < 0.02 |
| Test formulation treatment | M | 18 | 168.95 ± 51.45 | 185.66 ± 61.90 | 208.69 ± 57.28 | P < 0.01 |
| | F | 12 | 177.80 ± 45.73 | 193.65 ± 54.29 | 214.73 ± 49.32 | P < 0.01 |
| Conventional drug + test formulation treatment | M | 20 | 150.73 ± 42.80 | 188.90 ± 52.78 | 231.64 ± 65.04 | P < 0.001 |
| | F | 15 | 148.90 ± 50.82 | 173.45 ± 63.45 | 204.99 ± 59.72 | P < 0.001 |

Results of Invention:

The effect of test formulation evaluated in various experimental and clinical studies has exerted its beneficial role on various clinical and bio-chemical parameters under investigation. At baseline recordings after diagnosing the metabolic syndrome patients, a high values of BMI, blood pressure, different fraction of lipids (TC, TG, LDL-c and Apolipo B) were recorded and after 6 months of treatment significant reduction in the values were noticed. An increase in HDL cholesterol values indicated the cardio-protective role of test formulation. Though the conventional treatment has also shown better results on the bio-markers particularly lipid profile but considering the risk profile of conventional treatment the test formulation may be considered better option of treatment in the management of metabolic syndrome.

At baseline (before treatment) stage the level of adiponectin was found significantly low and leptin levels were higher in metabolic syndrome patients. The test formulation revealed adiponectin enhancing property in comparison to modern conventional treatment. Leptin level decreased following treatment given to various groups. During test period the endotheline level also reduced in treatment groups suggesting the reduced possibility of development of CHD as well as CHD mortality in metabolic syndrome patients.

At genetic level CD36 is one of the most important candidate gene also known as thrombospondin receptor, platelet collagen receptor. CD36 is responsible for membrane transport of long chain fatty acids into muscle and adipose tissues. CD36 is regulated by PPAR-γ and is a gene target of thiazolinediones and their upregulation appears to mediate insulin sensitizing activity. It is investigated in the present study that present test formulation upregulates the adipocytes and mediates the insulin sensitizing effects. Thus evaluating the CD36 in case of metabolic syndrome for understanding the status of insulin resistance, dyslipidemia and hypertension contributed for the development of a new drug entity (present plant based formulation) proposed a better remedial measure for the management of metabolic syndrome and risk of CVD in future.

On other hand the CD36 deficient individuals have impaired glucose disposal in response to insulin and increased levels of free fatty acids, triglycerides, fasting blood glucose and blood pressure suggesting the severity/seriousness of disease condition. On the whole the studies conducted suggests the risk between insulin resistance, obesity and hypertension that plays an important role in the pathogenesis of metabolic syndrome and thus is an important genetic markers to be utilized in the evaluation of a drug benefits in the management of metabolic syndrome.

It is to be noted that the present invention is susceptible to modifications, adaptations and changes by those skilled in the art. Such variant embodiments employing the concepts and features of this invention are intended to be within the scope of the present invention, which is further set forth under the following claims:

We claim:

1. A pharmaceutical capsule or tablet for the treatment of cardiovascular disease consisting essentially of therapeutically effective amounts of *Salacia parviflora*, *Tribulus terrestris*, and *Dioscorea glabra*.

2. The pharmaceutical capsule or tablet of claim 1, wherein *Salacia parviflora*, *Tribulus terrestris*, and *Dioscorea glabra* are hydro-alcoholic extracts.

3. The pharmaceutical capsule or tablet of claim 2, wherein the hydro-alcoholic extracts are obtained using a water to alcohol ratio of 70:30.

4. The pharmaceutical capsule or tablet of claim 1, wherein *Salacia parviflora* is *Salacia parviflora* root.

5. The pharmaceutical capsule or tablet of claim 1, wherein *Tribulus terrestris* is *Tribulus terrestris* fruit.

6. The pharmaceutical capsule or tablet of claim 1, wherein *Dioscorea glabra* is *Dioscorea glabra* rhizome.

7. The pharmaceutical capsule or tablet of claim 1,
wherein *Salacia parviflora* is *Salacia parviflora* root;
wherein *Tribulus terrestris* is *Tribulus terrestris* fruit; and
wherein *Dioscorea glabra* is *Dioscorea glabra* rhizome.

8. The pharmaceutical capsule or tablet of claim 2, wherein the therapeutically effective amount of *Salacia parviflora* hydro-alcoholic extract is between 250-550 mg.

9. The pharmaceutical capsule or tablet of claim 2, wherein the therapeutically effective amount of *Tribulus terrestris* hydro-alcoholic extract is between 225-450 mg.

10. The pharmaceutical capsule or tablet of claim 2, wherein the therapeutically effective amount of *Dioscorea glabra* hydro-alcoholic extract is between 250-500 mg.

11. The pharmaceutical capsule or tablet of claim 2,
wherein the therapeutically effective amount of *Salacia parviflora* hydro-alcoholic extract is between 250-550 mg;
wherein the therapeutically effective amount of *Tribulus terrestris* hydro-alcoholic extract is between 225-450 mg; and
wherein the therapeutically effective amount of *Dioscorea glabra* hydro-alcoholic extract is between 250-500 mg.

12. The pharmaceutical capsule or tablet of claim 11,
wherein *Salacia parviflora* is *Salacia parviflora* root;
wherein *Tribulus terrestris* is *Tribulus terrestris* fruit; and
wherein *Dioscorea glabra* is *Dioscorea glabra* rhizome.

13. The pharmaceutical capsule or tablet of claim 12, wherein the plurality of hydro-alcoholic extract have a water to alcohol ratio of 70:30.

14. The pharmaceutical capsule or tablet of claim 2,
wherein the therapeutically effective amount of *Salacia parviflora* hydro-alcoholic extract is 425 mg;
wherein the therapeutically effective amount of *Tribulus terrestris* hydro-alcoholic extract is 200 mg; and
wherein the therapeutically effective amount of *Dioscorea glabra* hydro-alcoholic extract is 325 mg.

* * * * *